United States Patent
Strub et al.

(10) Patent No.: US 7,374,387 B2
(45) Date of Patent: May 20, 2008

(54) METHOD AND ARRANGEMENT FOR EMPTYING BIG BAGS

(75) Inventors: Rolf Strub, Jongny (CH); Wan-Chang Chiu, Shin Chu (TW)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 75 days.

(21) Appl. No.: 10/574,765

(22) PCT Filed: Oct. 7, 2004

(86) PCT No.: PCT/EP2004/011222
§ 371 (c)(1),
(2), (4) Date: Apr. 6, 2006

(87) PCT Pub. No.: WO2005/039985
PCT Pub. Date: May 6, 2005

(65) Prior Publication Data
US 2007/0131303 A1 Jun. 14, 2007

(30) Foreign Application Priority Data
Oct. 10, 2003 (EP) .................................. 03022976

(51) Int. Cl.
*B65B 69/00* (2006.01)
(52) U.S. Cl. ..................................... 414/411
(58) Field of Classification Search ................ 414/411, 414/412
See application file for complete search history.

(56) References Cited

U.S. PATENT DOCUMENTS

| | | | |
|---|---|---|---|
| 3,664,530 A * | 5/1972 | Takiguchi | 414/412 |
| 3,811,586 A * | 5/1974 | Lavoie | 414/412 |
| 3,948,402 A * | 4/1976 | Schott, Jr. | 414/412 |
| 4,658,992 A * | 4/1987 | Peleus | 222/199 |
| 4,735,543 A * | 4/1988 | St. Lawrence | 414/421 |
| 4,953,752 A * | 9/1990 | Tousignant et al. | 222/23 |
| 5,405,053 A * | 4/1995 | Zublin | 222/83.5 |
| 5,613,824 A * | 3/1997 | Kato | 414/412 |
| 5,638,988 A * | 6/1997 | Rogers et al. | 222/81 |
| 5,649,801 A * | 7/1997 | White | 414/412 |
| 6,293,318 B1 * | 9/2001 | Schmidt et al. | 141/330 |

FOREIGN PATENT DOCUMENTS

NL 1015987 2/2002

* cited by examiner

*Primary Examiner*—Saul J. Rodriguez
*Assistant Examiner*—Joshua I Rudawitz
(74) *Attorney, Agent, or Firm*—Tyler A. Stevenson

(57) ABSTRACT

A method and an arrangement are provided for emptying a Big Bag or similar transport container which is filled with pourable, especially pulverized goods which are not to come into contact with their surroundings, wherein the Big Bag is inserted in a sluice means (2) which is closed off from the surroundings, with simultaneous sealing of the sluice means, which communicates with a processing container (3) for receiving the contents of the Big Bag, whereupon the Big Bag is cut open inside the sluice means by a cutting means (6) provided therein.

The empty Big Bag is compressed in a removal zone (A) inside the sluice means (2) and removed into a plastic sack (8) attached to the sluice means (2).

7 Claims, 5 Drawing Sheets

METHOD AND ARRANGEMENT FOR EMPTYING BIG BAGS

The invention relates to a method according to the preamble of claim 1 and an arrangement according to the preamble of claim 4.

A method and an arrangement of this kind is known fom NL-C-1 015 987, wherein over a Big Bag receiving holder having a rectangular cross-section, a ring-shaped structure is set down, by which the emptied Big Bag is pulled out of the receiving holder by means of arms and supplied, via a ring-shaped chamber, to a removing means fitted on the lower side of the ring-shaped structure.

Big Bags are sack-shaped transport containers of tear-resistant reinforced synthetic web material which have a volume of for example, one cubic meter and which are used for transporting, for example shipping, pourable goods. The Big Bags, which are provided with carrying loops, must be cut open for emptying, wherein it is difficult to transfer the pulverized goods contained therein into a container, such as a processing tank, such that no pulverized goods escape into their surroundings. This is especially a problem if the pulverized goods have properties which are detrimental to health and operating personnel can be exposed to danger during the emptying process.

It is the object of the invention to design a method and an arrangement of the kind mentioned above such as to simplify the insertion of the Big Bag into a sluice means for emptying.

This is achieved according to the invention by the characterizing features in claims 1 and 4. Because the Big Bag is inserted in the sluice means by a transporting unit which, when set down on the sluice means, seals this off from its surroundings, a simple structure of the arrangement results wherein the operating processes within the sluice means can be carried out by mechanical means, so that the manual work required is limited merely to hooking the delivered Big Bag onto the transporting unit and removing a sealed packaging container with the emptied Big Bag.

Figure 1:
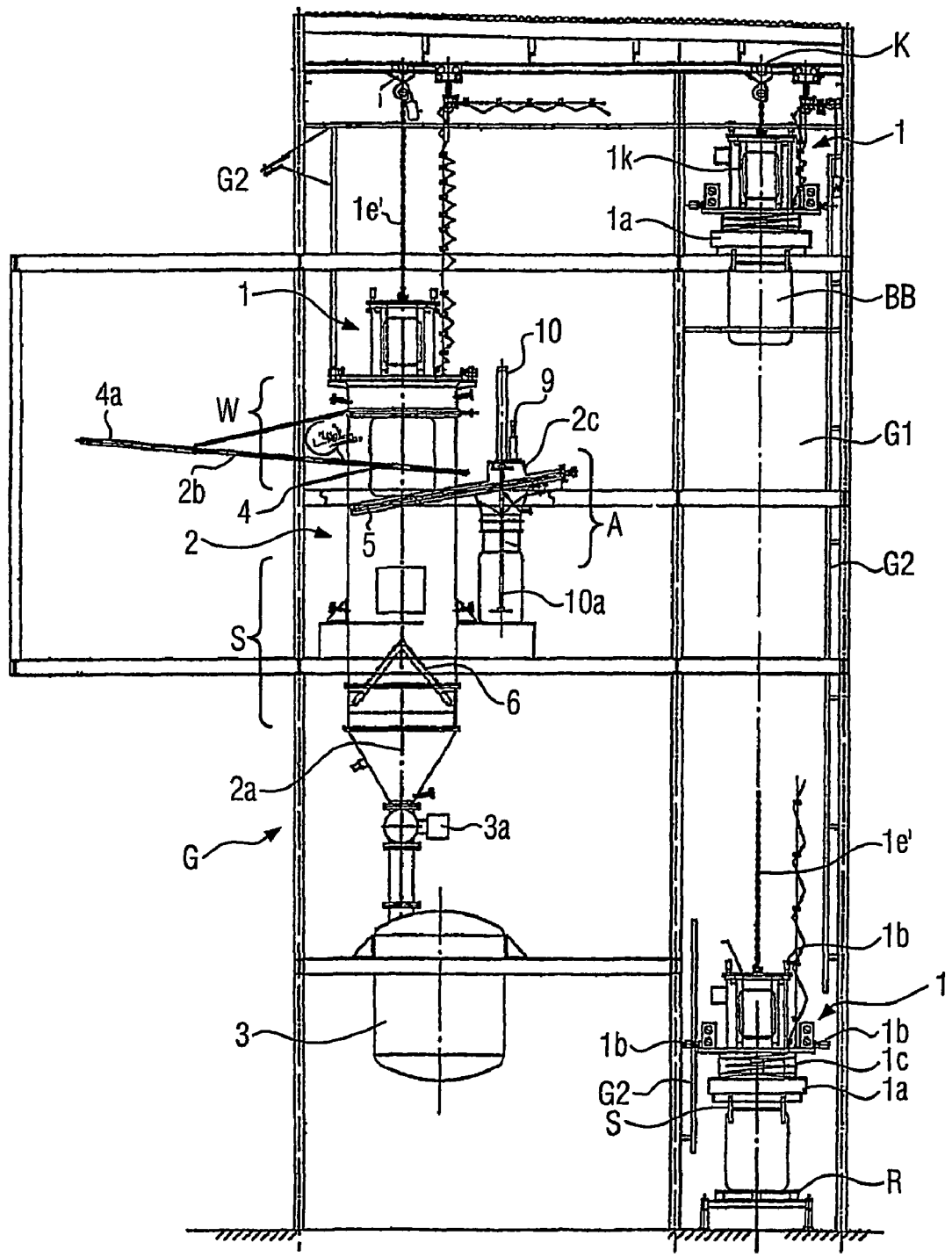
Figures 2, 2A:
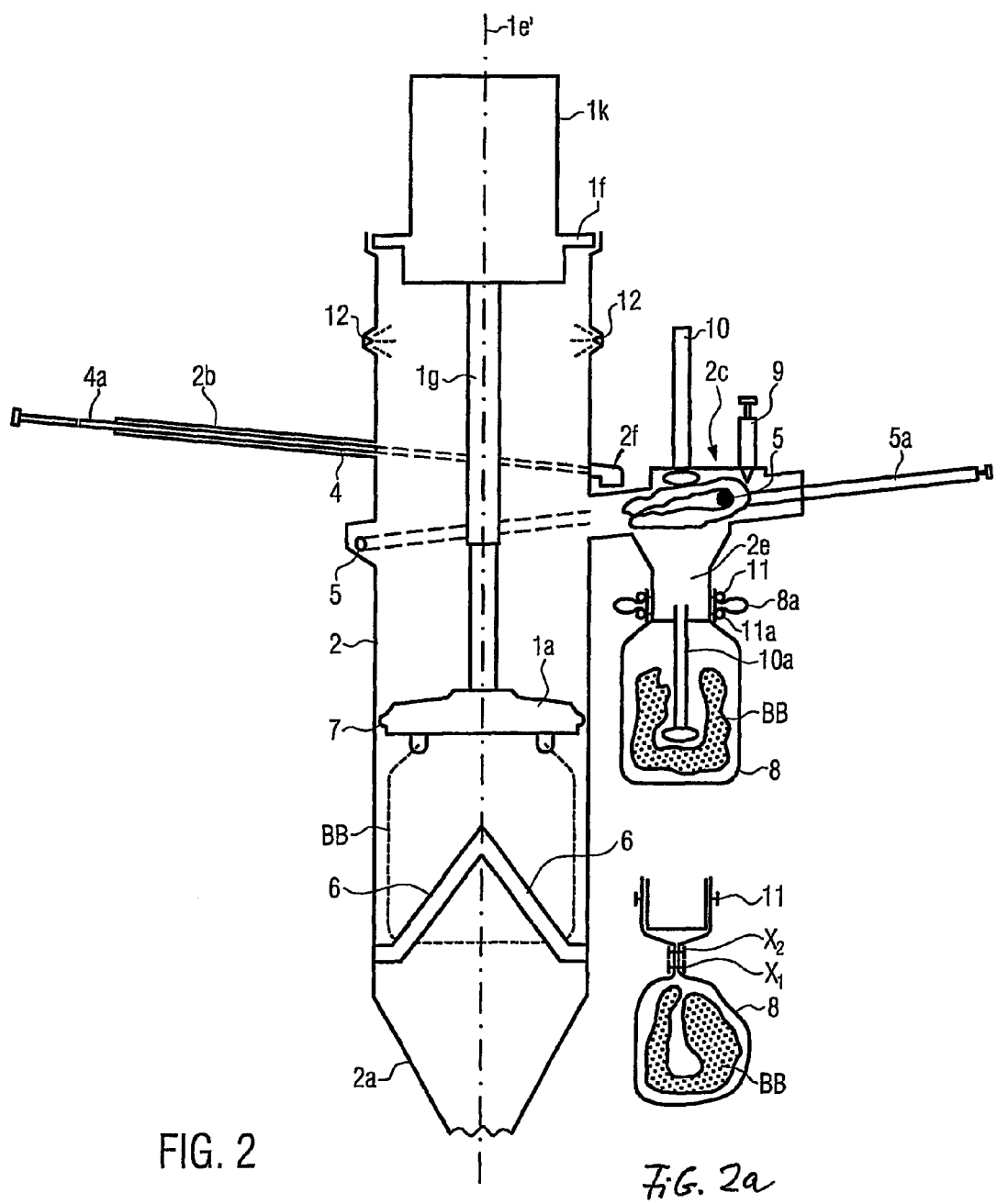
Figure 3:
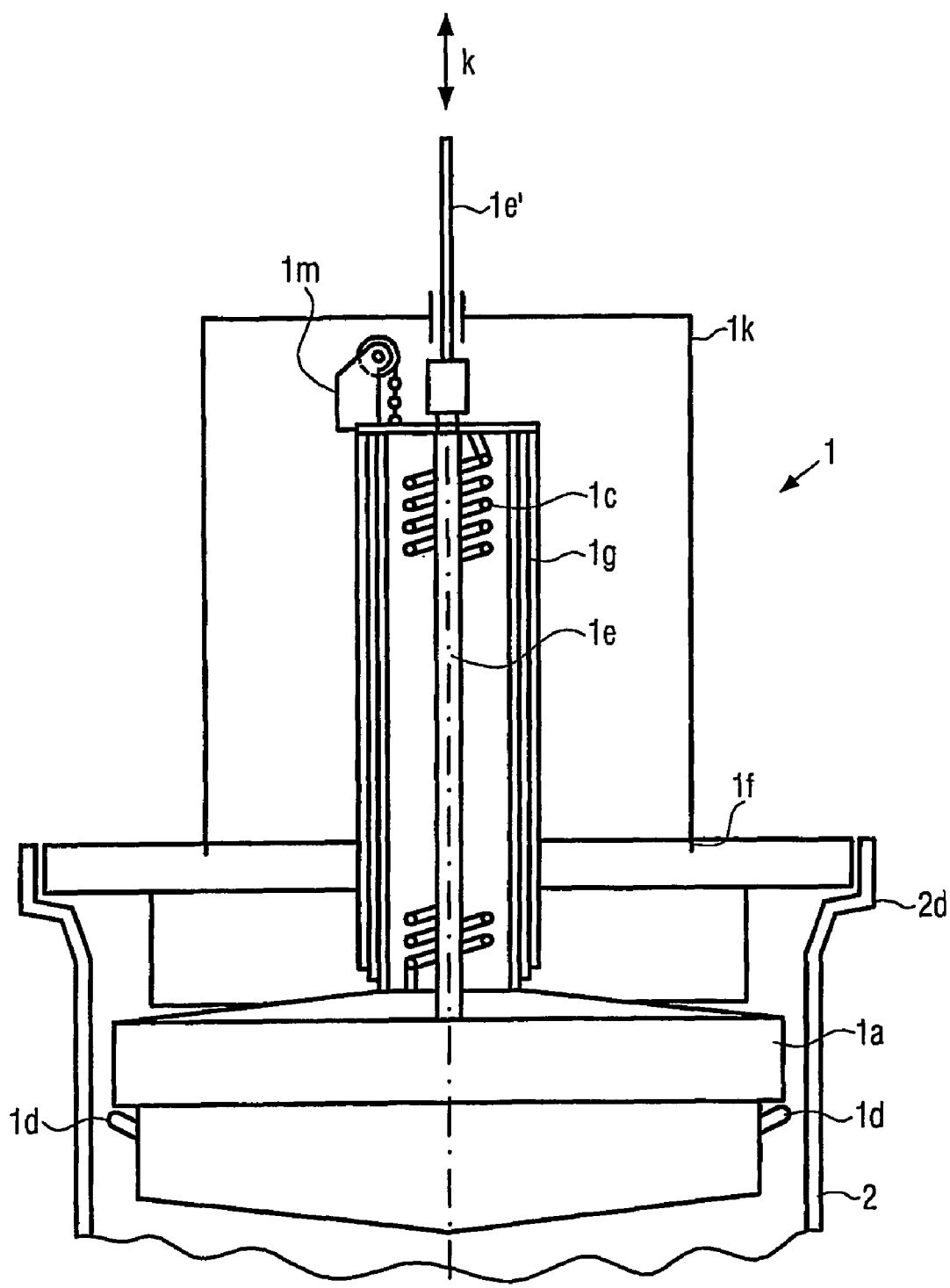
Figure 4:
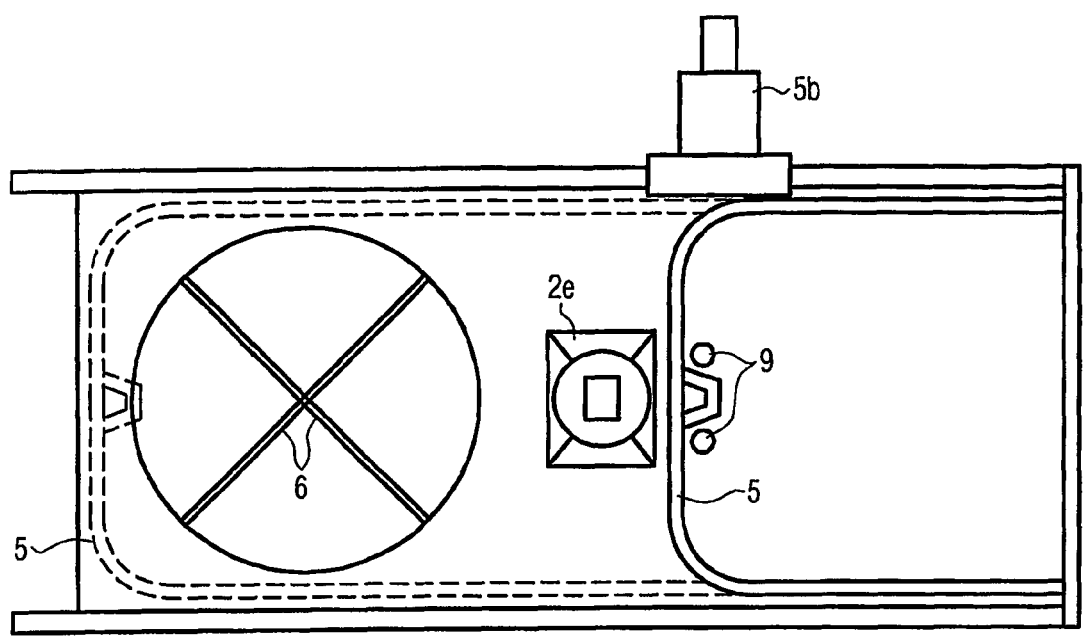
Figure 5:
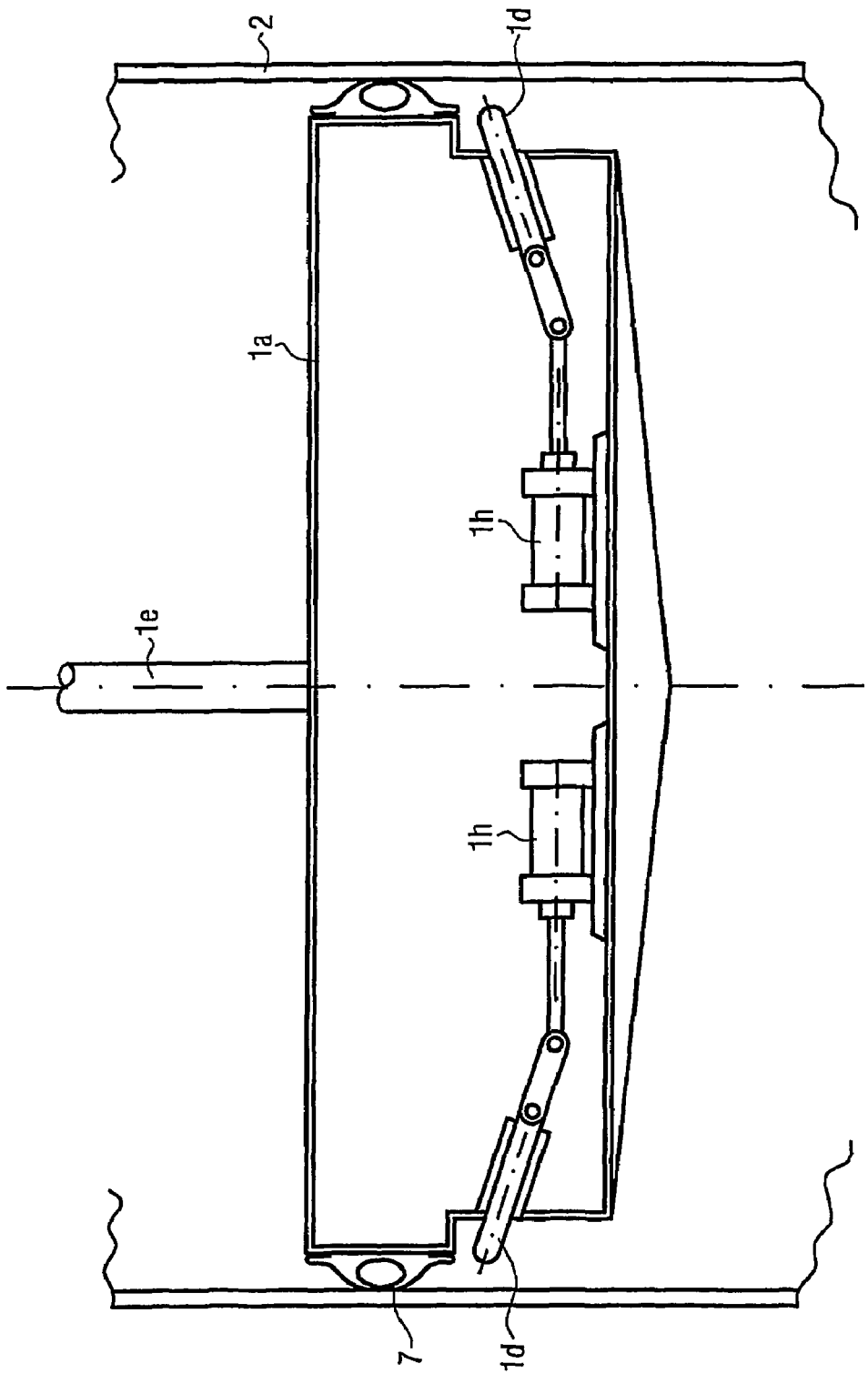

An exemplary embodiment of the invention is explained in more detail below with reference to the drawing, in which FIG. 1 shows a schematic sectional view of a tower-like building having the emptying arrangement housed therein, FIG. 2 shows a schematic representation of the emptying apparatus, FIG. 3 shows schematically the transporting unit during setting-down on the sluice means, FIG. 4 shows in a schematic plan view the principle of operation of a removing bow, and FIG. 5 shows the hooking-on means on the transporting plate of the transporting unit.

FIG. 1 shows schematically a tower-like building G having a transporting shaft G1 and an emptying apparatus arranged laterally to the transporting shaft. On a transport path, for example a roller path R, a Big Bag BB is inserted in the transporting shaft G1. The Big Bag is usually provided with four carrying loops S distributed around its upper circumference, which are manually hooked on a transporting plate 1a of a transporting unit 1, which is pulled upward in the transporting shaft G1 by a crane arrangement K as shown in FIG. 1. From the upper position, the transporting unit 1 is moved horizontally to the left in FIG. 1 over the emptying apparatus by the crane arrangement K, whereupon the transporting unit 1 is lowered until it comes to abut on the upper edge of a sluice means 2.

In the transporting shaft G1 and over the sluice means 2, guide rails G2 are laterally mounted, with which guide rollers 1b engage at the transporting unit 1 so that during the lifting and lowering movement of the transporting unit 1, this cannot twist. Additionally, at the top a horizontal guide rail G2 is provided, with which guide rollers 1b mounted on the top side of the transporting means 1 engage, so that the transporting unit also maintains the predetermined position during the horizontal transporting movement.

The sluice means 2 has an approximately tubular structure having an open upper end and a funnel 2a at the lower end, which is connected by means of a tube having a check valve 3a to a processing container, for example a stirring tank 3, in which the goods emptied from the Big Bag are processed or made available for further processing. While the transporting unit 1 is lifted up, the upper open end of the sluice means 2 is closed by a slider 4 which can be retracted from the tubular-shaped area of the sluice means 2 by a laterally protruding actuating means, for example a pneumatic cylinder 4a, before the transporting unit 1 having the Big Bag hooked thereon is set down on the open upper end of the sluice means 2. As FIG. 2 shows, the slider 4 is moveable into the open position in a laterally protruding closed guide 2b, wherein the closed guide is joined to the tubular section of the sluice means 2. Below the slider 4, at the tubular section of the sluice means 2, an area 2c is formed laterally in which a bow 5, explained in more detail below, is displaceable transverse to the tubular section of the sluice means 2, as FIG. 2 shows. In the lower area of the tubular section, above the funnel 2a a cutting means is provided in the form of inclined knives 6, by which the bottom of a Big Bag is cut open when placed on these knives.

As soon as the transporting unit 1 having the Big Bag hooked thereon is located over the sluice means 2, the slider 4 is displaced into the open position. The bow S is in the non-operating position on the left in FIGS. 2 and 4, outside the through-passageway area of the Big Bag. FIG. 3 shows schematically the placing of the transporting unit 1 on the off-set upper edge 2d of the tubular sluice means 2. The transporting plate 1a having laterally protruding carrying spikes 1d is directly joined by means of a rod link 1e then a cable 1e', or a chain or the like, to the crane arrangement K. Above the transporting plate 1a, a cylindrical structure 1k having a flange-shaped part If is arranged, whose outer edge comes to abut on the shoulder of the upper end 2d of the sluice means 2. When the transporting unit 1 having the flange 1f is set down on the sluice means 2, this is closed or sealed. Hereupon, the transporting plate 1a can be lowered by the crane arrangement, wherein a telescope means 1g, which surrounds the connecting rod 1e and the cable 1e', is moved out during the lowering movement. 1c designates a helix-shaped supply pipe for the transporting plate 1a, which is laid around the rod 1e.

The telescope means 1g is formed such that it guarantees the sealing of the inside of the sluice means 2 outwards in relation to the passage opening of the crane cable 1e or 1e', when nitrogen is introduced into the sluice means as explained below. Further, the telescope means 1g, which preferably has a rectangular cross-section, prevents twisting of the transporting plate 1a on the cable 1e during lowering of the transporting plate in the sluice means 2. Hereby, the diagonal positioning of the Big Bag on the knives 6 is guaranteed. Finally, the telescope means 1g also serves to protect the supply pipe 1c during the lifting and lowering movement of the transporting plate 1a in the sluice means.

Because the cable 1e of the crane arrangement K is directly jointed to the transporting plate 1a and the cylindrical structure 1k of the transporting unit 1 merely sits on the transporting plate 1a, the whole transporting movement of the transporting unit 1 outside the sluice means 2 and inside it is carried out by the crane arrangement K, wherein only a drive motor at the crane arrangement is necessary for all the transporting processes.

In the following, the emptying of a Big Bag filled with cyanuric chloride in powder form is described. After the upper area of the sluice means 2 is sealed in this way, the inside of the sluice means is made inert using nitrogen, wherein for example the oxygen content is reduced to less than 8% so that the risk of explosion when opening the Big Bag is excluded. Hereupon, the transporting plate 1*a* is lowered inside the sluice means 2 until the Big Bag is placed onto the knives 6, preferably using pressure, and is cut open. The contents of the Big Bag pour out downward via the funnel 2*a* into the stirring tank 3. Due to the Big Bag being moved up and down twice on the transporting plate 1*a*, complete emptying is guaranteed.

In a Big Bag having a content of 1*t* and dimensions of 1×1×1.2 m, the sluice means 2 has a diameter of approximately 1.5 m and a height of ca. 6.5 m. It has a fluid-impermeable structure and three zones:

a zone S for cutting open the bottom of the Big Bag by means of diagonally arranged knives 6, which diagonally cut open the bottom of the Big Bag so that complete emptying is guaranteed, a zone A, in which the empty Big Bag is fully automatically removed in a plastic bag 8 by the removing bow 5, and a zone W, in which the transporting plate 1*a* is washed and dried.

After being cut open, the empty Big Bag is lifted to the height of the removing bow 5, which is formed for example U-shaped for encompassing the Big Bag as FIG. 4 shows. By an actuating cylinder 5*a*, the removing bow 5 is drawn to the right in FIG. 2 over a funnel-shaped outlet 2*e*, on which a plastic sack 8 was tightly attached by hand before the start of the emptying process. Over the right-hand end position of the removing bow 5 in FIGS. 2 and 4, a cylinder 9 is arranged whose piston rod fixedly holds or clamps the Big Bag while the removing bow 5 is moved back into its starting position on the left-hand side in FIGS. 2 and 4. Over the funnelshaped outlet 2*e*, a cylinder 10 is arranged, whose piston rod 10*a* presses the empty Big Bag down into the plastic sack 8.

As FIG. 5 shows, at the transporting plate 1*a* there are mounted diametrically opposite fixing spikes 1*d*, which are each displaceable back and forth by pneumatic actuating cylinders 1*h*. Corresponding to the four carrying loops of a Big Bag, two such fixing spikes 1*d* are provided on each side. After the empty Big Bag is lifted up into the removal zone A, the two left-hand fixing spikes 1*d* in FIGS. 1 and 5 are retracted so that the Big Bag is released on the left-hand side, whereupon the pneumatic actuating cylinders 5*a* move the removing bow 5 approximately horizontally to the right. After the removing bow 5 has then transported the Big Bag a certain way to the right, the two righthand fixing spikes 1*d* are also retracted, so that the Big Bag is completely released and is now brought by the removing bow 5 alone into the position shown in FIG. 2 over the removal opening 2*e*.

As soon as the Big Bag has reached this position, it is held or clamped by preferably two pneumatic cylinders 9 arranged one behind the other, while the removing bow 5 is moved back into its non-operating position to the left in FIGS. 2 and 4. The removing bow 5 can also be moved horizontally by a drive motor 5*b* via a toothed rack, as FIG. 4 shows. Hereupon, the piston rod 10*a* of the pneumatic cylinder 10 is lowered and the Big Bag is pressed into the plastic sack 8 after the pneumatic cylinders 9 have released the Big Bag.

The plastic sack 8 is fixed by its upper edge through an upper fixing ring 11 to the wall of the funnel-shaped removal opening 2*e*. At a distance below this, a lower fixing ring 11*a* is provided, wherein the plastic sack 8 is connected to the removal opening 2*e* such that a sufficient length of the plastic sack is available between the two fixing rings 11 and 11*a*, which is indicated in FIG. 2 by a bulge 8*a*. Hereupon, the lower fixing ring 11*a* is released so that the plastic sack 8 drops down some way and the area of the plastic sack 8 present due to the overlength 8*a* can be manually tied off at a distance under the removal opening 2*e* at x1 (FIG. 2*a*). In this way, the plastic sack 8 containing the Big Bag is sealed airtight, whereupon between the tying-off position x1 and the removal opening a further tying-off x2 takes place, so that the plastic sack can be cut off between the two tying-off positions x1 and x2, while the removal opening 2*e* remains closed due to the remaining area of the plastic sack. The plastic sack 8 containing the Big Bag is hereupon disposed of for example by burning.

After or still during this removal process, the transporting plate 1*a* is pulled up into the washing zone W over the slider 4, whereupon the slider 4 is closed. In this area of the sluice means 2, washing jets 12 are provided distributed over the circumference (FIG. 2), through which xylene is sprayed in, and the transporting plate 1*a* is cleaned of traces of the contents of the Big Bag. Due to the inclined position of the slider 4, the xylene runs into a groove 2*f* inside the sluice means 2, which leads to the lower area thereof, so that the xylene washing liquid can be removed into the stirring tank 3. For cleaning, the transporting plate 1*a* can be led past the spray jets 12 for example twice. After the washing process, xylene drops are blown off by nitrogen, whereupon air-drying can be used.

Hereupon, the transporting plate 1*a* can be lifted by the crane K, wherein the cylindrical structure 1*k*) which lies on the transporting plate 1*a* and is carried by this, is lifted up with the transporting plate 1*a*.

The transporting unit 1 having the transporting plate 1*a* can hereupon be moved into the starting position for receiving a new Big Bag, while a new plastic sack 8 is manually attached to the removal opening 2*e*. Necessary manual work is therefore limited to hooking the carrying loops S of the full Big Bag on the fixing spikes 1*d*, and tying-off and removing the plastic sack 8 and fixing on a new plastic sack.

In FIG. 5, around the transporting plate 1*a* there is an inflatable membrane 7, by means of which the transporting plate 1*a* can be sealed off from the inside wall of the sluice means 2. In particular, this sealing off is performed when the Big Bag is in zone S for cutting open and emptying, as FIG. 2 shows. During the lifting and lowering movement of the transporting plate 1*a* inside the sluice means 2, the membrane 7 is preferably switched to unpressurized.

In FIG. 3, 1*m* designates a means having a chain which is joined to the transporting plate 1*a* and can be used for indicating the position of the transporting plate 1*a* relative to the sluice means 2. The indicating means itself is not shown in FIG. 3.

The arrangement described guarantees high operational safety, wherein the arrangement can be used without a gas mask, even if the Big Bag contains materials which are detrimental to health. Outside the building G, the emission of all odours can be stopped by operating the arrangement using slightly low pressure inside the building G.

Various modifications of the construction described are possible. For example, the sluice means can also be arranged substantially horizontally, wherein for cutting open the bottom of the Big Bag a knife means can be provided liftably or moveably inside the sluice means. Here, the removing bow 5 can, for example, be provided after the cutting means, for removing the empty Big Bag at the end of the sluice, while the transporting plate is moved back into a washing zone in front of the cutting means.

The invention claimed is:

1. Method for emptying a Big Bag which is filled with pourable, pulverized goods which are not to come into contact with the surroundings, comprising the following steps:

inserting the Big Bag from above into a substantially vertically arranged sluice means (2) which is sealable from the surroundings and communicates with a processing container (3) for receiving the contents of the Big Bag, cutting open the Big Bag inside the sluice means by a cutting means (6) arranged on the lower side of the sluice means, on which the Big Bag is placed, and transferring the empty Big Bag to a removal zone (A) in the sluice means, in which the Big Bag is compressed and removed into a plastic sack (8) attached to the sluice means (2), characterized in that the Big Bag is inserted into the sluice means by a transporting unit (1), which transporting unit (1) comprises on its lower side a transporting plate (1a) for carrying the Big Bag, which transporting plate is connected to a crane arrangement by a cable (1e) so that the transporting plate with the Big Bag is lowered by the crane arrangement within the sluice means and the transporting unit, by being set down on the sluice means, seals the sluice means off from its surroundings after removal of the Big Bag from the sluice means, a part (1a) of the transporting unit (1) transporting the Big Bag inside the sluice means (2) is lifted into a washing zone (W) over a slider (4), by which the sluice means (2) is sealed off, while the part (1a) of the transporting unit is washed by spray jets (12) and then dried.

2. Method according to claim 1, wherein the empty Big Bag is lifted inside the tubular sluice means into a removal zone (A) and pushed laterally by a removing bow (5) over a removal opening (2e), under which the plastic sack (8) is attached.

3. Arrangement for emptying a Big Bag, which is filled with pourable, pulverized goods which are not to come into contact with the surroundings, comprising a sluice means (2) which is sealable from its surroundings in a fluid-impermeable way, is arranged substantially vertically, and has at its lower end a cutting means (6), wherein the sluice means is joined to a processing container (3) for the contents of the Big Bag, a removing means (5, 10) by which, over a removal opening (2e), the empty Big Bag is compressed and expelled characterized in that a transporting unit (1) for the Big Bag is provided with a transporting plate (1a) mounted on its lower side for carrying the Big Bag, which transporting plate is connected to a crane arrangement by a cable (1e) so that the transporting plate with the Big Bag can be lowered by the crane arrangement within the sluice means and the transporting unit (1), by being placed on the sluice means (2), seals the sluice means off from the surroundings over the removing means (5, 10), in the sluice means (2) a slider (4) is provided, over which a washing zone (W) for the transporting plate (1a) is formed.

4. Arrangement according to claim 3, wherein the removing means has a removing bow (5) which is horizontally moveable inside the sluice means (2) and under whose end position the removal opening (2e) is formed in a lateral projection (2c) of the sluice means.

5. Arrangement according to claim 4, wherein over the removal opening (2e), there are provided at least one cylinder (9) for clamping the Big Bag and at least one cylinder (10) for expelling the Big Bag after its release by the clamping cylinder (9).

6. Arrangement according to claim 3, wherein the slider (4) is arranged inclined for directing a washing liquid off.

7. Arrangement according to claim 3, where between the transporting plate (1a) and a part (1k) of the transporting unit (1) resting on the sluice means (2), a telescope means (1g) is provided, which seals off the inside of the sluice means (2) from the outside and prevents twisting of the transporting plate (1a) during the lifting and lowering movement inside the sluice means (2).

* * * * *